US012623060B2

(12) United States Patent
    Ebner et al.

(10) Patent No.: US 12,623,060 B2
(45) Date of Patent: May 12, 2026

(54) CATHETER INSERTION DEVICE WITH IMPROVED FLASHBACK RESPONSE

(71) Applicant: ICU Medical, Inc., Plymouth, MN (US)

(72) Inventors: Timothy Ebner, Plymouth, MN (US); Kathryn Felicito, Plymouth, MN (US); Harsh Chheda, Plymouth, MN (US)

(73) Assignee: ICU MEDICAL, INC., San Clemente, CA (US)

( * ) Notice: Subject to any disclaimer, the term of this patent is extended or adjusted under 35 U.S.C. 154(b) by 1029 days.

(21) Appl. No.: 17/737,145

(22) Filed: May 5, 2022

(65) Prior Publication Data

US 2022/0370764 A1     Nov. 24, 2022

Related U.S. Application Data

(63) Continuation of application No. 16/811,714, filed on Mar. 6, 2020, now Pat. No. 11,439,794.

(Continued)

(51) Int. Cl.
    *A61M 25/00*          (2006.01)
    *A61B 5/15*           (2006.01)
    (Continued)

(52) U.S. Cl.
    CPC ..... *A61M 25/0693* (2013.01); *A61B 5/15003* (2013.01); *A61M 25/0097* (2013.01); *A61M 25/0606* (2013.01); *A61M 25/0618* (2013.01)

(58) Field of Classification Search
    CPC .......... A61M 25/0693; A61M 25/0097; A61M 25/0606; A61M 25/0618; A61M 25/0102; A61B 5/15003
    See application file for complete search history.

(56) References Cited

U.S. PATENT DOCUMENTS 3,335,723 A     8/1967   Waldman
3,352,306 A    11/1967   Hirsch
                (Continued)

FOREIGN PATENT DOCUMENTS

EP          0993839        4/2000
JP       2006055674        3/2006
                (Continued)

OTHER PUBLICATIONS

EPO Search Report dated Feb. 24, 2023for EP application No. 20764919.5.

(Continued)

*Primary Examiner* — Chelsea E Stinson
*Assistant Examiner* — Hamza A Darb
(74) *Attorney, Agent, or Firm* — Louis Woo

(57)                ABSTRACT

In various embodiments, an improved catheter insertion device is described that provides an improved flashback response and use for deep vein access. In various embodiments, the improved flashback response comprises two separate and distinct flash events, the first indicating insertion of a cannula in a blood vessel, and a second indicating insertion of a catheter in the blood vessel. The two flash responses are made possible by a combination of features provided on the cannula, such as including a view window in the cannula and a flat relief portion on the outer surface of the cannula at the distal opening.

8 Claims, 7 Drawing Sheets

Related U.S. Application Data

(60) Provisional application No. 62/815,066, filed on Mar. 7, 2019.

(51) Int. Cl.
    *A61M 25/01*      (2006.01)
    *A61M 25/06*      (2006.01)

(56) References Cited

U.S. PATENT DOCUMENTS

| | | | |
|---|---|---|---|
| 4,755,356 A | 7/1988 | Robbins et al. | |
| 5,697,014 A | 12/1997 | Brimhall | |
| 6,497,994 B1 | 12/2002 | Kafrawy | |
| 6,527,747 B2 | 3/2003 | Adams et al. | |
| 7,736,337 B2 | 6/2010 | Diep et al. | |
| 8,979,803 B2 | 3/2015 | Darr | |
| 2002/0107483 A1 | 8/2002 | Cook | |
| 2003/0105431 A1 | 6/2003 | Howell | |
| 2004/0215146 A1 | 10/2004 | Lampropoulos et al. | |
| 2004/0267200 A1 | 12/2004 | Carlyon et al. | |
| 2005/0015071 A1 | 1/2005 | Brimhall | |
| 2005/0075606 A1 | 4/2005 | Botich et al. | |
| 2007/0093778 A1* | 4/2007 | Cindrich | A61M 5/158 |
| | | | 604/500 |
| 2008/0300543 A1 | 12/2008 | Abriles et al. | |
| 2010/0305519 A1 | 12/2010 | McKinon et al. | |
| 2011/0054402 A1 | 3/2011 | Tanabe et al. | |
| 2011/0054403 A1 | 3/2011 | Tanabe et al. | |
| 2012/0136311 A1 | 5/2012 | Knutsson | |
| 2012/0323181 A1 | 12/2012 | Shaw et al. | |
| 2014/0221977 A1* | 8/2014 | Belson | A61M 25/0606 |
| | | | 604/509 |
| 2015/0151084 A1 | 6/2015 | Braun | |
| 2016/0106959 A1 | 4/2016 | Woehr | |
| 2016/0175563 A1* | 6/2016 | Woehr | A61M 25/0606 |
| | | | 604/168.01 |
| 2016/0220161 A1 | 8/2016 | Goral et al. | |
| 2016/0220791 A1 | 8/2016 | Akcay et al. | |
| 2016/0228683 A1 | 8/2016 | Tietze | |
| 2016/0310704 A1 | 10/2016 | Braun | |
| 2016/0354539 A1 | 12/2016 | Tan et al. | |
| 2017/0120010 A1 | 5/2017 | Burkholz et al. | |
| 2018/0028788 A1 | 2/2018 | Belson | |
| 2018/0339131 A1 | 11/2018 | Muse et al. | |
| 2019/0038876 A1* | 2/2019 | Isaacson | A61M 5/3286 |

FOREIGN PATENT DOCUMENTS

| | | |
|---|---|---|
| WO | 9325253 | 12/1993 |
| WO | 9614894 | 5/1996 |
| WO | 1999052584 | 10/1999 |
| WO | 2001056642 | 8/2001 |
| WO | 02096495 A2 | 12/2002 |
| WO | 2002096494 | 12/2002 |
| WO | 2007050788 A2 | 5/2007 |
| WO | 2017074677 A1 | 5/2017 |
| WO | 2017074684 | 5/2017 |
| WO | 2018164769 A1 | 9/2018 |

OTHER PUBLICATIONS

USPTO; Non-Final office action dated Mar. 24, 2021 in U.S. Appl. No. 16/486,126.

USPTO; Non-Final office action dated Apr. 13, 2021 in U.S. Appl. No. 16/486,108.

ISA; International Search Report and Written Opinion PCT application No. PCT/US18/021135 dated May 16, 2018.

ISA; International Search Report and Written Opinion PCT application No. PCT/US18/021143 dated May 11, 2018.

ISA; International Search Report and Written Opinion PCT application No. PCT/US18/021155 dated Apr. 27, 2018.

ISA; International Search Report and Written Opinion PCT application No. PCT/US2020/021485 dated May 5, 2020.

EUIPO; Search report dated Sep. 24, 2020 in EP application No. 18763871.3.

EUIPO; Search report dated Sep. 27, 2020 in EP application No. 18764834.0.

* cited by examiner

CATHETER INSERTION DEVICE WITH IMPROVED FLASHBACK RESPONSE

CROSS-REFERENCE TO RELATED APPLICATIONS

This application is a continuation of U.S. patent application Ser. No. 16/811,714 filed Mar. 6, 2020, now U.S. Pat. No. 11,439,794B2 issued Sep. 13, 2022, which claims priority to and the benefit of U.S. Provisional Patent Application Ser. No. 62/815,066 filed Mar. 7, 2019 and entitled "Catheter Insertion Device with Improved Flashback Response." The respective disclosures of the '714 application and the '066 provisional application are incorporated herein by reference in its entirety for all purposes.

FIELD OF INVENTION

The present disclosure generally relates to intravenous (IV) catheters and more particularly to catheter insertion devices that provide an improved blood flashback response during deep vein access.

BACKGROUND OF INVENTION

Clinical evidence regarding peripheral intravenous catheters has shown the adoption of closed system catheters (with an integrated extension set) may reduce complications, extend catheter indwell, and reduce the cost of care. As clinicians adopt closed system catheters it's desirable that new devices include features and functions that are known to be useful in connection with successful peripheral IV catheter (PIVC) insertion.

One such feature is early indication of vascular entry. While PIVCs can include a flash chamber, it takes time for blood to flow through the length of the cannula and into the flash chamber. For this reason, PIVCs today may include a more distally oriented flashback feature that provides earlier indication of entry within the catheter tube.

A common method to provide this functionality is to create a window, or fenestration, through the wall of the cannula to visualize blood before it becomes visible in the flash chamber. Intuitively, the distance between the cannula fenestration and the distal opening of the cannula is minimized to provide the fastest flashback response. Additionally, the cannula fenestration may be positioned in proximity to the distal opening of the cannula to reduce the likelihood of blood leakage, especially when the cannula is withdrawn from the catheter through a blood control seal or self-sealing septum. However, distal placement of a cannula fenestration creates a challenge when clinicians place an IV into a deep vein, or in an obese patient, as it can be difficult to see the flash in the cannula fenestration when the catheter is inserted deep under the skin.

Therefore, there continues to be an ongoing need for new catheter devices that balance the speed of the flashback response, the risk of blood leakage, and the proximal visibility of the flashback response for deep vein access.

SUMMARY OF INVENTION

In various embodiments of the present disclosure, a catheter insertion device comprises a cannula having distally oriented features that operate in combination to provide two consecutive and visible flashback responses, separate from the flash visible in the flash chamber. The first flashback response upon entry of the cannula bevel into a blood vessel and the second flashback response upon entry of the catheter into the blood vessel. These features may be applied to a device with or without an additional flash chamber The catheter insertion device is usable with both closed system catheters and open system catheters having a blood control seal.

In various embodiments, a catheter insertion device comprises: a catheter hub comprising a catheter extending distally from the catheter hub to a distal end, the catheter having an outer surface and an inner surface defining a fluidic passageway therethrough, the catheter hub comprising an interior cavity and a septum contained therein; a cannula axially movable through the septum and the catheter, the cannula having an outer surface, an inner surface defining a central bore therethrough, and a distal opening in the shape of a bevel ending distally at a sharp distal tip; and a view window in the cannula, the view window comprising a fenestration in the cannula through to the central bore and a transparent seal member fit over the fenestration, the fenestration having a proximal edge and a distal edge on the outer surface of the cannula defining an axial length of the fenestration; wherein an annular space is present between the inner surface of the catheter and the outer surface of the cannula when the cannula is within the fluidic passageway of the catheter.

In various embodiments, the transparent seal member is selected from a transparent film, transparent insert, transparent sleeve or transparent cover.

In various embodiments, the cannula further comprises a narrower diameter portion surrounding the fenestration such that the transparent seal member fit therein provides a viewing capsule capable of filling with fluid present in the cannula.

In various embodiments, the transparent seal member comprises a glass or plastic sleeve having substantially similar dimensions to the narrower diameter portion, and wherein the outer diameter of the cannula remains substantially constant over the viewing capsule.

In various embodiments, the proximal edge of the fenestration is spaced apart from the sharp distal tip by a distance $D_1$ from about 10 mm to about 50 mm.

In various embodiments, the distal end of the catheter is tapered such that a circumferential seal is present between the inner surface of the catheter and the outer surface of the cannula at the distal end of the catheter when the distal opening of the cannula extends distally beyond the distal opening of the catheter.

In various embodiments, the cannula further comprises a flat relief portion extending proximally on the cannula by a length $D_3$ beginning from a position proximal to the distal opening of the cannula and providing a fluidic pathway under said seal for blood to flow proximally into the annular space.

In various embodiments, the length $D_3$ of the flat relief portion is from about 10 mm to about 50 mm to accommodate the location and size of the cannula fenestration.

In various embodiments, a catheter insertion device comprises: a catheter hub comprising a catheter extending distally from the catheter hub to a distal end, the catheter having an outer surface and an inner surface defining a fluidic passageway therethrough, the catheter hub comprising an interior cavity and a septum contained therein; a cannula axially movable through the septum and the catheter, the cannula having an outer surface, an inner surface defining a central bore therethrough, and a distal opening in the shape of a bevel having a length $D_4$ and ending distally at a sharp distal tip; and a fenestration radially disposed through a wall of the cannula into the central bore of the cannula, the fenestration having a proximal edge and a distal edge on the outer surface of the cannula defining an axial length of the fenestration; wherein an annular space is present between the inner surface of the catheter and the outer surface of the cannula when the cannula is within the fluidic passageway of the catheter; wherein a distance $D_1$ between the sharp distal tip of the cannula and the proximal edge of the fenestration is greater than the length of the septum; and wherein a distance $D_2$ between the sharp distal tip of the cannula and the distal edge of the fenestration is less than the length of the septum.

In various embodiments, $D_1$ is less than or equal to 150% of the septum length, and $D_2$ is greater than $D_4$ such that the distance $D_1$ remains less than or equal to 150% of the septum length.

In various embodiments, the septum comprises a self-sealing septum.

In various embodiments, the distal end of the catheter is tapered such that a circumferential seal is present between the inner surface of the catheter and the outer surface of the cannula at the distal end of the catheter when the distal opening of the cannula extends distally beyond the distal opening of the catheter.

In various embodiments, the cannula further comprises a flat relief portion extending proximally on the cannula by a length $D_3$ beginning from a position proximal to the distal opening of the cannula and providing a fluidic pathway under said seal for blood to flow proximally into the annular space.

In various embodiments, the cannula further comprises a circumferentially enlarged portion positioned between a proximal end of the flat relief portion and the distal edge of the fenestration providing a seal between the outer surface of the cannula and the inner surface of the catheter within the annular space.

In various embodiments, an intravenous method comprises: inserting a cannula into a blood vessel, the cannula having an outer surface, an inner surface defining a central bore therethrough, a distal opening, and a view window comprising a fenestration in the cannula through to the central bore and a transparent seal member fit over the fenestration; observing a blood flash in the view window of the cannula confirming insertion of the distal opening of the cannula into the blood vessel; inserting a distal end of a catheter into the blood vessel by distally moving the catheter relative to the cannula, the catheter extending distally from a catheter hub to the distal end, the catheter having an outer surface and an inner surface defining a fluidic passageway therethrough, the catheter hub comprising an interior cavity and a septum contained therein, the catheter coaxially arranged over the cannula to provide an annular space between the outer surface of the cannula and the inner surface of the catheter; and observing a blood flash in the annular space confirming insertion of the distal end of the catheter into the blood vessel.

In various embodiments, a flat relief portion is included on the distal end of the cannula, the flat relief portion providing a fluidic pathway under a seal present between the inner surface of the catheter and the outer surface of the cannula at the distal end of the catheter, allowing blood to flow from the blood vessel into the annular space when the tip of the catheter enters the blood vessel.

In various embodiments, the flat relief portion extends proximally on the cannula by a length $D_3$ beginning from a position proximal to the distal opening of the cannula, wherein $D_3$ is from about 10 mm to about 50 mm.

In various embodiments, the distal end of the catheter is tapered to provide the seal.

In various embodiments, the cannula further comprises a narrower diameter portion surrounding the fenestration such that the transparent seal member fit therein provides a viewing capsule capable of filling with fluid present in the cannula, providing visual confirmation of insertion of the distal opening of the cannula into the blood vessel.

In various embodiments, the blood vessel is a deep vein.

BRIEF DESCRIPTION OF THE FIGURES

The subject matter is pointed out with particularity and claimed distinctly in the concluding portion of the specification. A more complete understanding, however, may best be obtained by referring to the detailed description and claims when considered in connection with the following drawing figures:

DETAILED DESCRIPTION OF THE INVENTION

Figure 1:
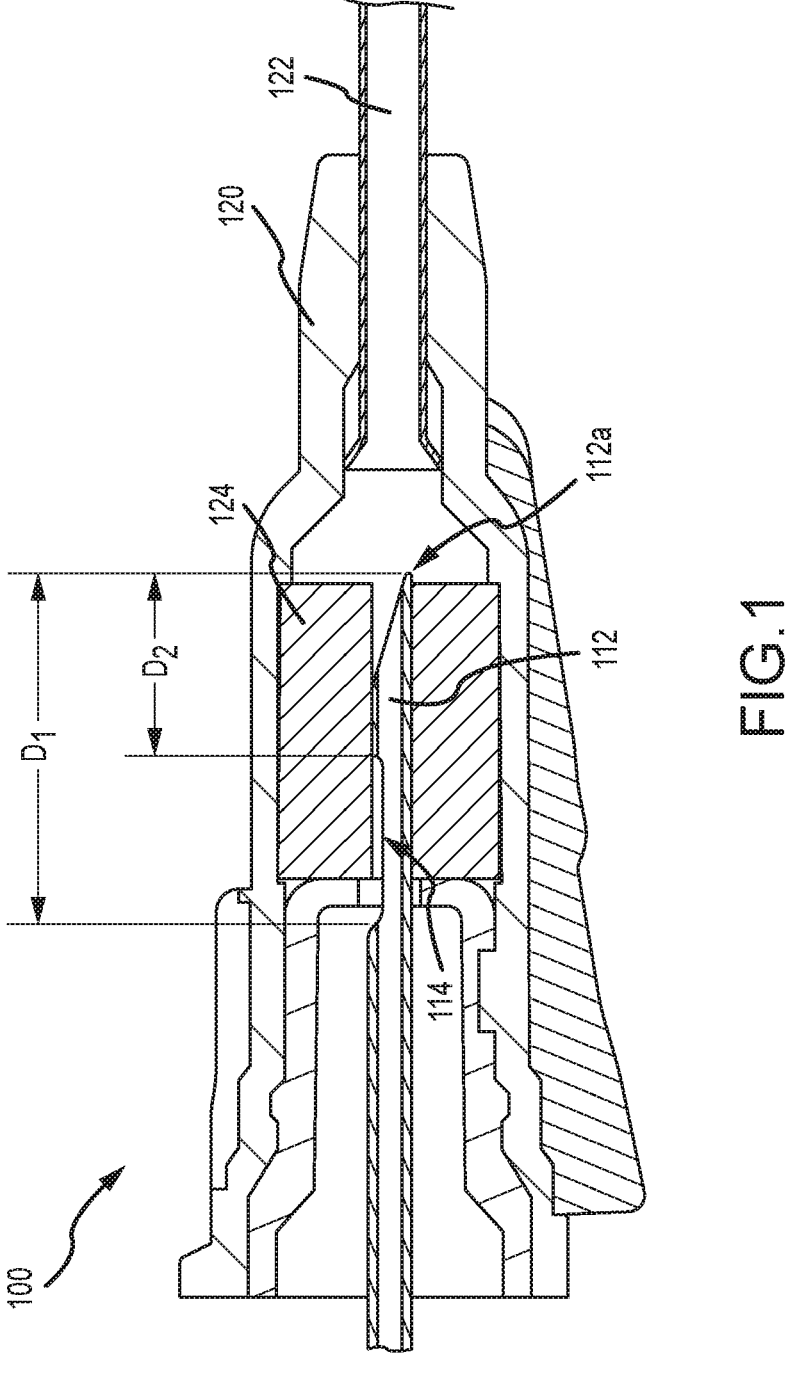
FIG. 1 illustrates a catheter insertion device in accordance with various embodiments, having a fenestration in a cannula and showing a position during proximal withdrawal of the cannula into a septum.

The detailed description of various embodiments herein references the accompanying drawings, which show various embodiments by way of illustration. While these various embodiments are described in sufficient detail to enable those skilled in the art to practice the disclosure, it should be understood that other embodiments may be realized, and that logical, chemical, mechanical and structural changes may be made without departing from the spirit and scope of the disclosure. Thus, the detailed description herein is presented for purposes of illustration only and not of limitation.

In various embodiments of the present disclosure, an improved catheter insertion device is described. The catheter insertion device comprises a catheter tube and a cannula disposed concentrically and moveable therein, wherein the cannula comprises a flat relief portion and a fenestration. The fenestration and the flat relief portion in the cannula act in concert to provide a dual flashback response, a first response when the cannula enters a vessel and a second response when the catheter enters the vessel. In various embodiments, the fenestration may be open to provide blood flow therethrough, or closed with a transparent seal member and configured as a viewing window. The dimensions of both the flat relief portion and the fenestration on the cannula, and the relative positioning of the two features, are optimized for rapid flashback response and reduced blood leakage when the catheter insertion device is used in accessing deeply set veins, or accessing blood vessels in obese individuals.

Definitions and Conventions

As used herein, the term "proximal" refers to a location of a portion of a device or an end of a device closest to a user of the device. Consequently, the term "distal" refers to a location of a portion of a device or an end of a device furthest from a user of the device. For example, a hypodermic syringe has a sharp needle tip at its distal end and a plunger at its proximal end. The terms are also associated with direction, movement and relative positioning, whereby "proximally" generally refers to movement or relative positioning closer to the user and "distally" generally refers to movement or relative positioning further away from the user.

As used herein, the term "fenestration" refers to a radially disposed opening, notch, aperture or hole radially disposed through a sidewall in a cannula, extending from the exterior of the cannula through to the fluid passageway running axially inside the cannula, i.e., the central bore. Thus, a fenestration in a cannula provides a fluid port out a side of the cannula provided the fenestration is not covered up in some fashion to prevent the blood exit. In various embodiments, a cannula may comprise a fenestration, but the fenestration is covered with a transparent seal member, whereby the fenestration functions as a viewing window and not as a fluid exit port. The term fenestration is not meant to be limited as to how the radial opening was created in the cannula. For example, a cannula may have been molded with a fenestration, or some of the side wall of a cannula may have been removed, such as drilled through, cut out, ground away, torched or otherwise ablated to create the fenestration. In various embodiments, a fenestration in a cannula may have various shapes and dimensions, e.g., may comprise a circular hole radially through into the core of the cannula, or the fenestration may be more of a trough or trench, thus having an axial length greater than the diameter of the cannula. A fenestration configured as a trough comprises a proximal edge and a distal edge, which are each part of the wall of the cannula. The distance between these edges along the length of the cannula defines a length to the fenestration.

As used herein, the terms "transparent" and "nontransparent" refer to properties of a material or a structure and the ability for an operator to see through or not be able to see through the material or the structure with the naked eye. For example, an operator would not be able to see into a metal cannula, but could be able to see into a clear plastic cannula, such as to determine if fluid is flowing through the cannula. Nontransparent should not be confused with metallic, since a non-metallic material, like plastic, could be made nontransparent with a pigment in the plastic to block transparency. Transparent is used generally to include translucent.

As used herein, the term "transparent seal member" refers to a transparent seal used over or beneath the fenestration to convert what would otherwise be an open port in the cannula into a viewing window to see blood moving into and/or through the cannula. A transparent seal member, used in this way, may comprise a thin film, like a shrink wrap, or a clear plastic flexible sleeve or clear plastic or glass insert. In various embodiments, a viewing window may comprise a fenestration sealed with a transparent shrink wrapped film. In more complex embodiments, a viewing window may comprise a fenestration fit with a plastic or glass insert. In various aspects, a narrowed diameter portion of a cannula around the location of a fenestration allows use of a tubular cover over the fenestration to provide a viewing window along that portion of narrower diameter, circumferentially around the cannula shaft. With a viewing window thus configured, blood does not fully exit into the catheter.

As used herein, the term "cannula" refers to a long tubular structure having an outer surface and an inner surface defining a fluidic passageway axially therethrough, such as an insertion needle having a particular gauge and a bore for fluid flow. In various embodiments, a cannula may comprise plastic or metal, and may include a sharp distal tip (e.g., a beveled end), along with a proximal end fitted into a cannula hub or other structure to facilitate handling and movement of the cannula relative to the catheter and catheter hub. In various embodiments, to retract a cannula proximally, a user may hold on to the catheter hub and pull the cannula proximally.

As used herein, the term "catheter" refers to a tube with an outer surface and an inner surface defining a fluidic bore of sufficient diameter such that the catheter can fit over the cannula like a sheath. In various embodiments, a catheter herein is a short section of clear plastic tubing acting as a sheath over the cannula when a catheter device comprising both cannula and catheter is in the ready position. In various embodiments, the catheter may include a taper at the distal opening such that the fit between the circumferential opening at the distal end of the catheter against the outer surface of the cannula is tighter than the fit between the catheter and cannula at other locations between these coaxially arranged elements. In various embodiments, a cannula can be withdrawn proximally through and entirely out from the catheter, such as after the catheter is positioned within a blood vessel and the cannula is no longer needed. In various embodiments, an annular (or interstitial) space is present between the outer surface of the cannula and the inner surface of the catheter such that the cannula and be axially moved within the catheter and blood flow is possible within this annular space. An elongated diameter portion on a cannula may be used to close off the interstitial space and block blood flow between the cannula and catheter.

With reference to FIG. 1, a catheter insertion device 100 in accordance with various embodiments of the present disclosure is illustrated in a cross-sectional view. Catheter insertion device 100 can be part of a closed or open catheter system. Example embodiments of catheter insertion device 100 comprise a cannula 112, a catheter hub 120, and a catheter 122 fit into and fluidically connected with the catheter hub 120. The cannula 112 comprises a distal end, which may comprise a sharp distal tip, and a proximal end that may terminate in a cannula hub (not illustrated in FIG. 1). The cannula hub, cannula 112, catheter hub 120, and catheter 122 can each be comprised of various plastics and/or metals used in the medical device industry.

In various embodiments, catheter hub 120 is a structure to which a catheter 122 is connected or which otherwise secures catheter 122. Catheter 122 can extend distally from a distal end of catheter hub 120 out to an open distal end. Catheter hub 120 and catheter 122 can each have a lumen extending there through, the lumen of catheter hub 120 being in communication with the lumen of catheter 122.

In various embodiments, catheter hub 120 comprises an inner cavity and a septum 124 contained therein, through which cannula 112 can pass. In various embodiments, the septum 124 comprises part of a closed system catheter or a blood control seal for an open system catheter. In various embodiments, the septum 124 comprises an elastomeric material such as silicon rubber. Septum 124 may further comprise a slit therethrough and any number of internal voids. FIG. 1 illustrates a position of the cannula 112 within the septum 124 during use of the catheter insertion device, at a moment in time when the cannula 112 is being withdrawn proximally through the septum 124.

In various embodiments, the cannula hub is a structure to which a cannula 112 is connected or which otherwise secures cannula 112. Cannula 112 can extend distally from a distal end of the cannula hub. Cannula 112 can be a conventional intravenous needle, an insertion needle, a cannula, a trocar or the like, and correspondingly, the cannula hub may be a needle hub that associates with a proximal portion of the catheter hub 120.

In various embodiments, cannula 112 comprises at least one fenestration 114. As illustrated in FIG. 1, the fenestration 114 appears as a trough extending through a wall of cannula 112, and having a measurable length axially along the cannula. In some embodiments, fenestration 114 is a void defined in part by proximal and distal edges of a wall of cannula 112, having a width approximating the diameter of the cannula and an axial length defined by D1-D2, i.e., the distance measured axially between the proximal edge and the distal edge of the wall of the cannula 112. The distal edge of fenestration 114 is spaced apart from the distal tip 112*a* of the beveled opening of the cannula 112 by a distance D2. In various aspects, distance D1 is less than or equal to 150% of the septum 124 length, and distance D2 is greater than the length of the bevel on the distal cannula (exemplified in FIG. 2B as D4), such that distance D1 remains less than or equal to 50% greater than the length of the septum 124. Specific dimensions for D1 and D2 are driven by the length of the septum 124 and the cannula bevel.

In various embodiments, and with continued reference to FIG. 1, fenestration 114 can be sealed and positioned proximally or extended proximally in length, forming a viewing window, in order to optimize flash visualization during deep vein access while preventing blood leakage, as explained herein below. In the context of a sealed viewing window rather than an open fenestration, the proximal aspect of the fenestration, defined by D1, and axial length of the fenestration, defined by D1-D2 in FIG. 1, need not be constrained in relation to the length of the septum 124 because the sealed fenestration reduces risk of blood leakage. In the case of a sealed fenestration for deep vein access, distance D1 may be about 10 mm to about 50 mm and may vary to accommodate needle lengths and gauge sizes. This range accommodates visualization of the flash window in shallow and deep veins. Distance D1-D2 may vary with cannula gauge and length. In various embodiments, the length of fenestration 114 can be extended proximally without concomitant lengthening or shortening of the distance D2. In other aspects, the fenestration 114 may be positioned more remote from the distal opening of the cannula 112, such as to provide space axially along the cannula for another feature to be present on the cannula between the cannula distal opening and the fenestration.

In various embodiments, the distance D1 between the distal opening of cannula 112 and the proximal edge of fenestration 114 is greater than the length of septum 124. However, as the length of D1 becomes significantly longer than the length of the septum, the risk of blood leakage through the septum while the cannula is proximally withdrawn increases when the fenestration is not sealed into a view window. If D1 is equal to or less than 150% of the septum length, a fluidic pathway through the septum, from the distal opening of the cannula out the proximal edge of the fenestration 114, appears at only a brief instance in time, during the proximal withdrawal of the cannula through the septum.

In various embodiments, the distance D2 between the distal opening of cannula 112 and the distal edge of fenestration 114 is greater than the length of the distal cannula bevel and less than the length of septum 124, as long as the length of the fenestration, i.e., D1-D2, is greater than 0.127 mm (0.005 inches), and distance D1 is less than or equal to 150% of the septum 124 length.

During use, cannula 112 is withdrawn proximally through the septum 124 from a beginning position where both the distal opening of the cannula 112 and the fenestration 114 are fully distal to and entirely outside the distal side of the septum 124, to a second position where both the distal opening of the cannula 112 and the fenestration 114 are fully proximal to and entirely outside the proximal side of the septum 124. Between these extremes, and when distance D1 is longer than the length of the septum 124 and distance D2 is less than the length of the septum 124, the fenestration 114 will either be fully occluded by septum 124 when the distal opening of the cannula 112 is entirely distal to the septum 124, or will at least be partially occluded by septum 124 when the distal opening of the cannula 112 is partially occluded by the septum 124. As the cannula 112 is withdrawn further in the proximal direction, the fenestration 114 will never be fully proximal to the septum 124 (and thus entirely open to the inner cavity of the catheter hub) until the distal opening of cannula 112 is fully within and thus sealed by septum 124. Such a configuration of features, and their relative dimensions, mitigates bypass flow through the septum by ensuring that fenestration 114 and the distal opening of the cannula 112 are simultaneously completely open only when both features are distal to the septum. In this way, the available flow path and potential for blood to leak through the septum 124 via a bypass route through the cannula 112 and out the fenestration 114 is controlled. Such embodiments may improve visibility of the flash response in deep vein access while controlling blood leakage. To minimize blood leakage, distance D1 is less than or equal to 150% of the length of the septum 124, and distance D2 is as small as possible without compromising the cannula bevel. Extending the length of the septum 124 may allow for greater distance D1 while mitigating blood leakage and optimizing visibility of the flash window in deep vein access.

Figures 2A, 2B:
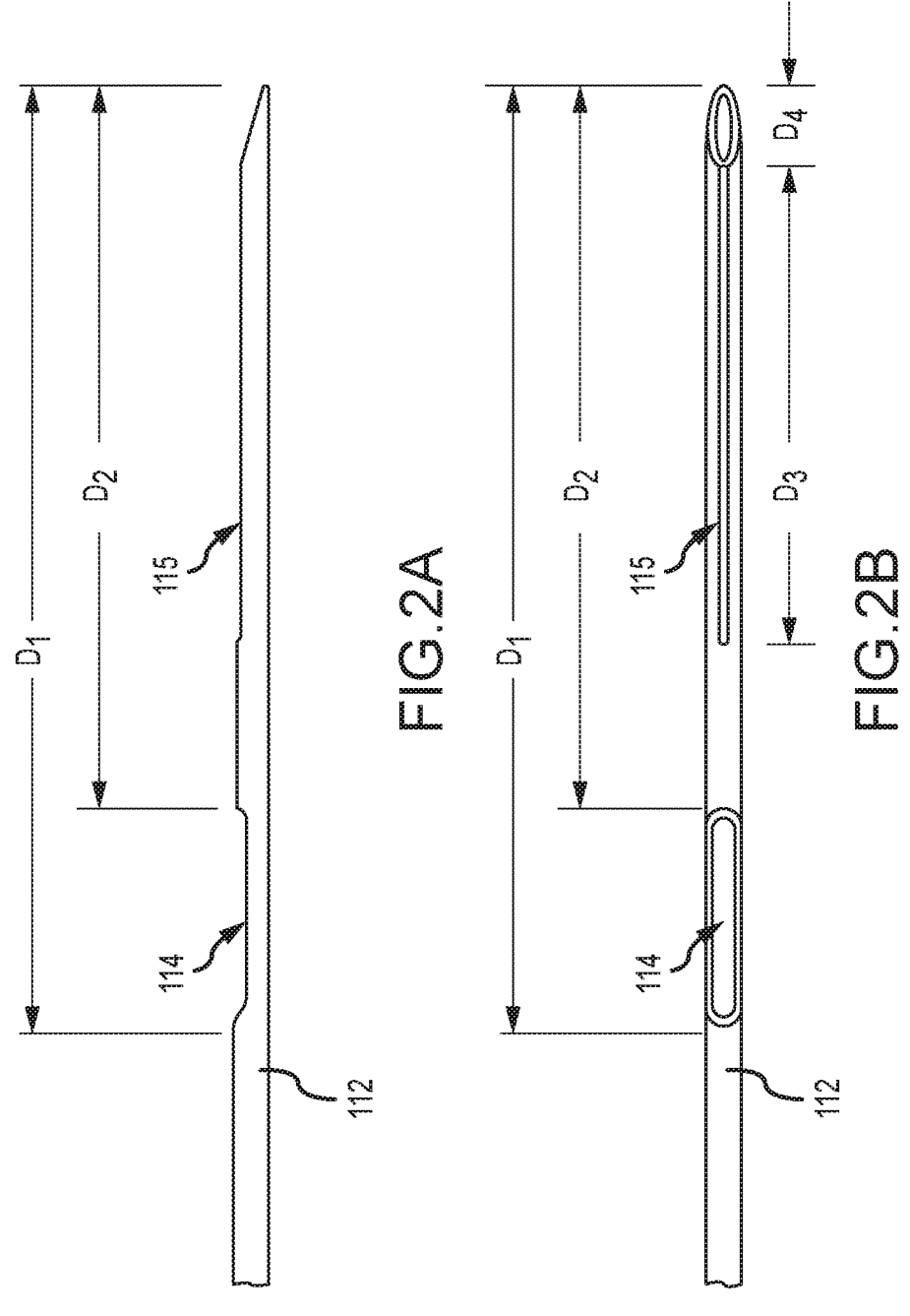
FIGS. 2A and 2B illustrate side and top views of a cannula in accordance with various embodiments, having a fenestration and a flat relief portion in relative spatial orientation.

FIGS. 2A and 2B illustrate side and top views, respectively, of a cannula in accordance with various embodiments of the present disclosure. As illustrated, when sealed, fenestration 114 may be spaced proximally at a significant distance from the distal opening of cannula 112, closer to the catheter hub than the distal opening of cannula 112. This configuration may improve visibility in deep vein access. In this embodiment the distance D2 from the distal opening of cannula 112 to the distal edge of fenestration 114 is greater than the length of septum 124 and incorporates a sealed fenestration acting as a viewing window.

In connection with an extended D2 length, cannula 112 can be modified to include a flat relief portion 115 extending proximally from the bevel of cannula 112, or from a location just proximal to the bevel of the cannula 112, axially toward the fenestration 114. The extended distance D2 as discussed provides room for such a flat relief portion 115 on the cannula 112. The cannula fenestration 114 provides a viewing window that indicates cannula entry in the vein, the flat portion 115 enables blood to enter the annulus between the catheter and cannula upon insertion of the catheter into the vein. In various embodiments, the length D3 of the flat relief portion 115 is from about 10 mm to about 50 mm. In general, flat relief portion 115 creates space between the inner diameter of catheter 122 and the outer diameter of flat portion 115 so blood will become visible as catheter 122 enters the vasculature. Stated differently, flat portion 115 can define, or embodiments of the present disclosure can otherwise comprise, an opening between the otherwise close fitting distal opening of catheter 122 against the outer diameter of cannula 112, (best seen in FIGS. 4A-4D). In particular, the distal end of the catheter 122 may be tapered such that the catheter 122 is essentially sealed around the outer diameter of the cannula 112. A flat relief portion 115 provides a shunt through this circumferential seal.

Flat portion 115 can be a portion of cannula 112 that, whether due to formation, removal or compression (e.g., flattening) of material or some other process, comprises a smaller diameter than an adjacent portion of cannula 112 without such a flat relief, but does not extend through a wall of the cannula 112 such as to create any sort of fluidic opening. In various embodiments, such as illustrated in FIGS. 2A, 2B, 3A, 3B, and 4A-4C, the flat relief portion 115 may begin just proximal to the distal opening of the cannula 112 and terminate prior to the distal edge of fenestration 114. In other embodiments not illustrated, flat relief portion 115 may extend distally through the beveled distal end of cannula 112. In other embodiments, and illustrated in FIG. 4C (element 118) and discussed below, cannula 112 may further comprise a bumped-out or enlarged transition, comprising for example a ferrule fit over a portion of the cannula 112. As discussed below, the enlarged portion can be positioned between the flat relief portion 115 and the fenestration 114 to block backward (distal) blood flow between the catheter 122 and cannula 112 so that all of the available flash indicator flows proximally to where a clinician can see it and there is discernable flash between the distal flat portion of the cannula and the fenestration.

In use, flash may be a visible signal to two separate and distinct events. For example, a first blood flash appears in fenestration 114 upon cannula 112 entry, followed by a second flash visible in catheter 122 upon catheter 122 entry. By leveraging these features of the cannula 112, clinicians receive a visual indication of cannula entry, then a separate indication of catheter entry. Such embodiments may provide a flash system that confirms cannula entry to prevent blowing-out the vein, and confirms catheter entry to help improve successful catheter advancement.

Figure 2C:
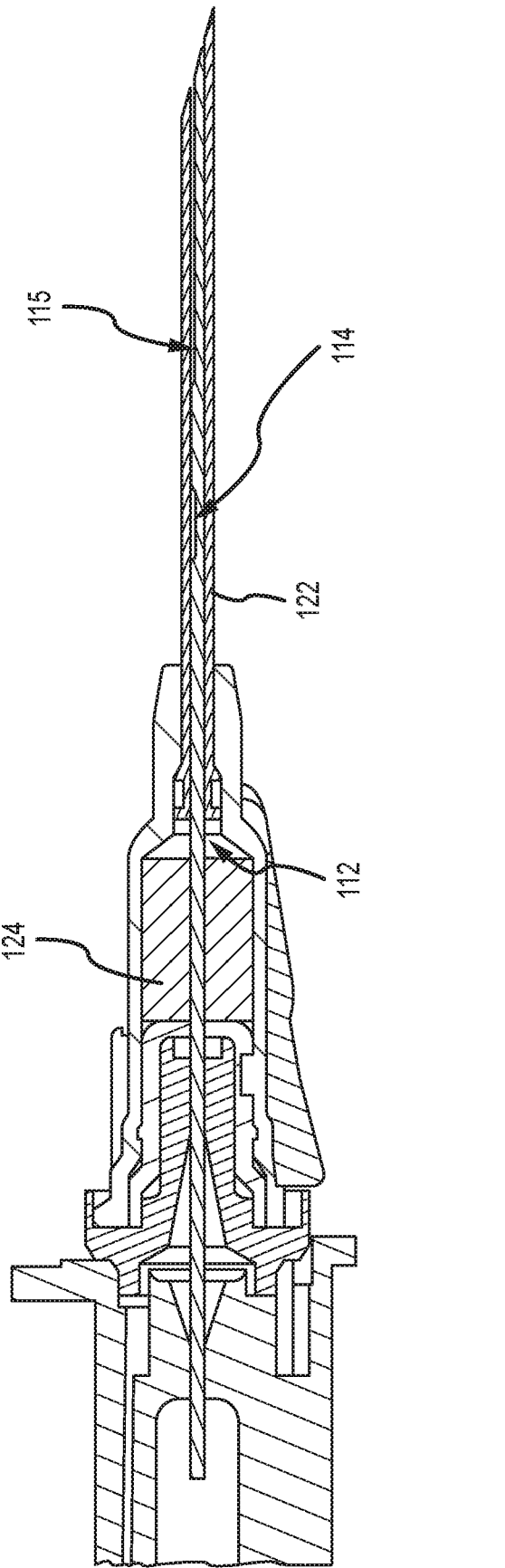
FIG. 2C illustrates a catheter insertion device in accordance with various embodiments, having a cannula comprising the features illustrated in FIGS. 2A and 2B.

FIG. 2C illustrates a complete catheter insertion device comprising a modified cannula 112 further comprising both a fenestration 114 open to blood flow therethrough, and a flat relief portion 115 to open blood flow between catheter and cannula.

Figures 3A, 3B:
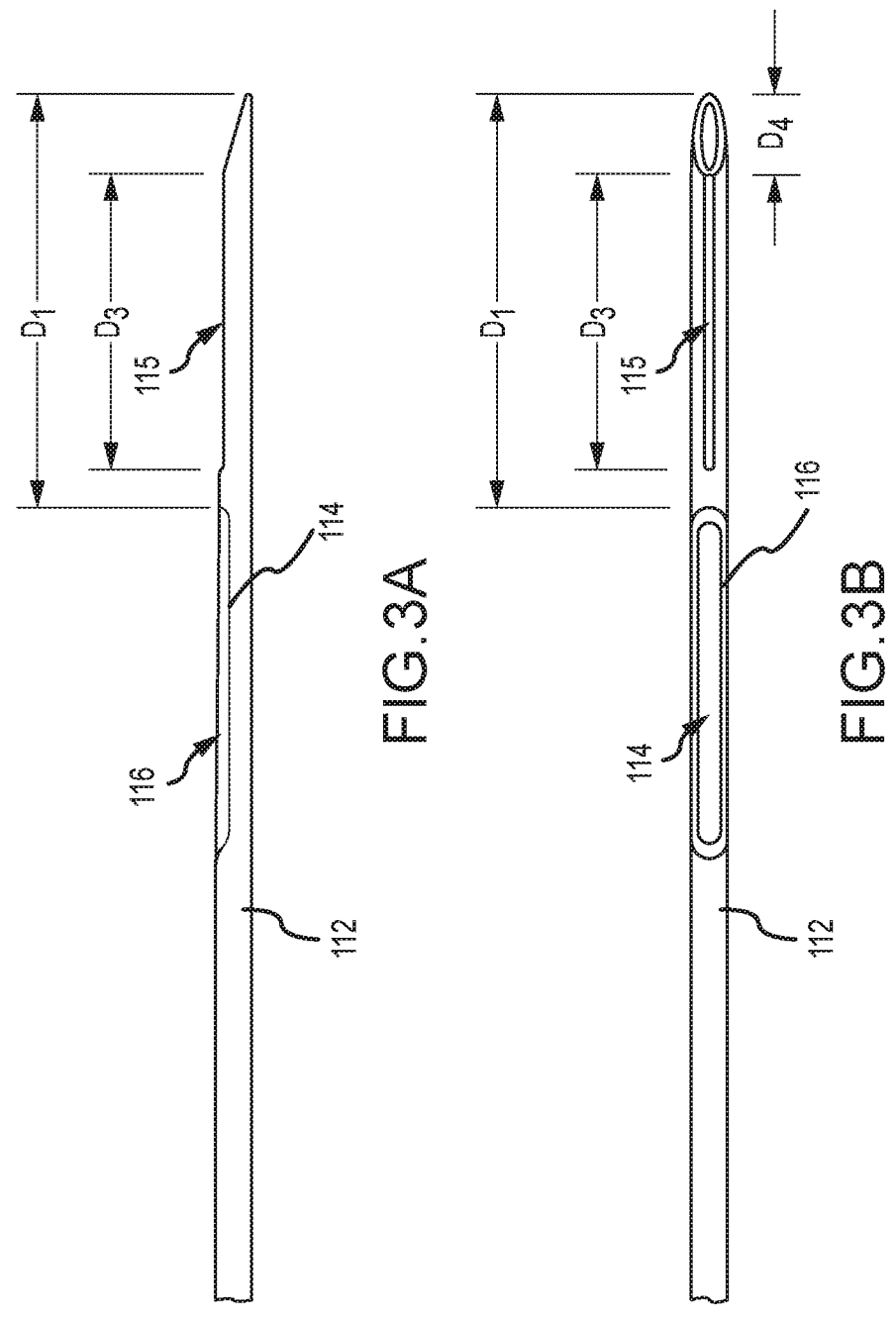
FIGS. 3A and 3B illustrate side and top views of a cannula in accordance with various embodiments, having a view window comprising an elongated fenestration sealed with a transparent seal member, and a flat relief portion in relative spatial orientation.

FIGS. 3A and 3B illustrate side and top views, respectively, of another cannula 112 in accordance with various embodiments of the present disclosure comprising versions of a view window rather than an open fenestration. In various embodiments, a viewing window comprises a fenestration 114 covered by a transparent seal member 116 such that the fenestration can no longer function as an open port into the annular space between cannula and catheter. In various embodiments, a transparent seal member for the fenestration is selected from a transparent film, a transparent insert, a transparent sleeve, and a transparent cover. In various aspects, a transparent film or insert are intended to seal the fenestration around its periphery. A transparent sleeve or cover may seal the fenestration around its periphery or at locations proximal and distal to the fenestration to provide a viewing capsule, depending on the nature of the sleeve or cover and whether a narrower diameter portion of the cannula is provided around the fenestration for the sleeve or cover to fit into.

As illustrated in FIGS. 3A and 3B, fenestration 114 in cannula 112 may be elongated and sealed with a transparent seal member 116, thus providing a long viewing window that allows clinicians to visualize blood within cannula 112 without having a blood flow pathway out through an open fenestration and a potential for blood leakage through the septum upon cannula withdrawal. In various embodiments, transparent seal member comprises a transparent film 116 sealingly positioned over the fenestration 114, such as a shrink-wrap shrunk tight around the circumference of the cannula 112, covering the entirety of the fenestration 114 and converting the open fenestration into a long and narrow viewing window (discussed in reference to FIG. 4A below). The shrink-wrap 116 may be only a few mils thick such that the transition in diameter from uncovered cannula to shrink-wrapped cannula is not a hinderance to the operation of the catheter insertion device. In other variations, transparent film 116 may be on the inside of the cannula 112, expanded against the open fenestration to seal it from the underside.

In other variations, the seal member for the fenestration may comprise a glass or a plastic cover or tubular sleeve or sheath, or a transparent insert having substantially similar dimensions and contours to the fenestration 114, wherein the transparent insert may be fit into the outline of the fenestration 114 like a car windshield fit into its corresponding window trim. In this regard, a transparent insert can be positioned relative to an inner lip around and slightly inside the circumference of the opening of fenestration 114. The lip may be a recessed feature around the opening of the fenestration, like a ledge into which the transparent insert can be fit and sealed therein. This configuration provides a smooth transition from the cannula over the viewing window with no change in diameter in the cannula. In further variations, the transparent seal member may comprise a transparent cover such as in the form of a tubular sleeve positioned on a portion of the cannula 112 that includes fenestration 114. Such a clear, tubular sleeve can be adhered and sealed around the cannula 112 to seal the fenestration 114 around its periphery. In other variation, the transparent cover comprises a sleeve having smaller diameter than the cannula 112, so that the clear sleeve can fit inside the central bore of the cannula 112, where it is expanded and sealed against the inside periphery of the fenestration 114.

In various embodiments, (and discussed in reference to FIG. 4B below), a portion of the cannula 112 around the fenestration 114 comprises a narrower diameter compared to the remainder of the cannula, such that a transparent cover 117 can be fit into this narrower diameter portion, sealing the cannula 112 at the distal and proximal ends of the narrower diameter portion, rather than sealing around the periphery of the fenestration. This configuration provides a viewing "capsule" into which a minimal amount of blood (microliters) can flow from the fenestration 114. Since the viewing capsule is sealed around the cannula 112, blood cannot flow out from the viewing capsule and into the annular space between catheter 122 and cannula 112.

In other embodiments, (and discussed in reference to FIG. 4D below), rather than having fenestration 114 sealed with either a sealing transparent film 116 or transparent cover 117 such as an interior or exterior sleeve, a length of cannula 112 can be made out of transparent material. In various embodiments, a nontransparent section of cannula 112 can be axially connected end-to-end with a transparent section of cannula 112, wherein the entirety of the transparent section acts as a long flash viewing window. In various embodiments, the nontransparent section and the transparent section may be friction fit together, such as with one portion having a tapered end to fit into the end of the other portion.

In accordance with embodiments comprising a sealed fenestration providing a viewing window or capsule, the fenestration 114 may be very long, extending down a length of cannula 112, or very small located in proximity to catheter hub 120, without any possible risk of blood leakage. Optionally, embodiments comprising a sealed fenestration 114 can also comprise a flat relief portion 115, as described herein. In such an embodiment, cannula 112 may prevent blood from entering catheter 122 through fenestration 114, while allowing blood into the space between the cannula and catheter through the distal flat 115. In this way, the penetration of the cannula into the vein would be indicated by visualizing blood through the cannula window, and entry of the catheter into the vein would be indicated by visualizing blood in the catheter tube.

Figure 3C:
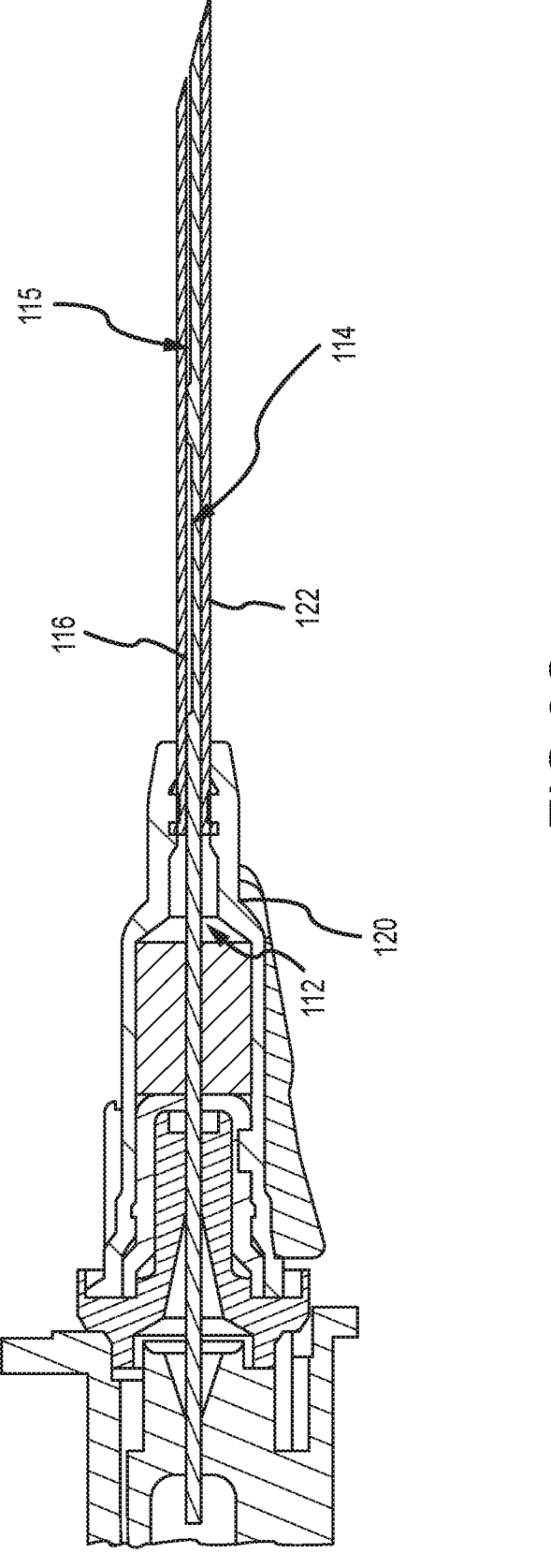
FIG. 3C illustrates a catheter insertion device in accordance with various embodiments, having a cannula comprising the features illustrated in FIGS. 3A and 3B.

FIG. 3C illustrates a complete catheter insertion device comprising a modified cannula 112 further comprising both a covered and elongated fenestration 114 acting as a view window, and a flat relief portion 115 to open blood flow between catheter and cannula.

Figure 4A:
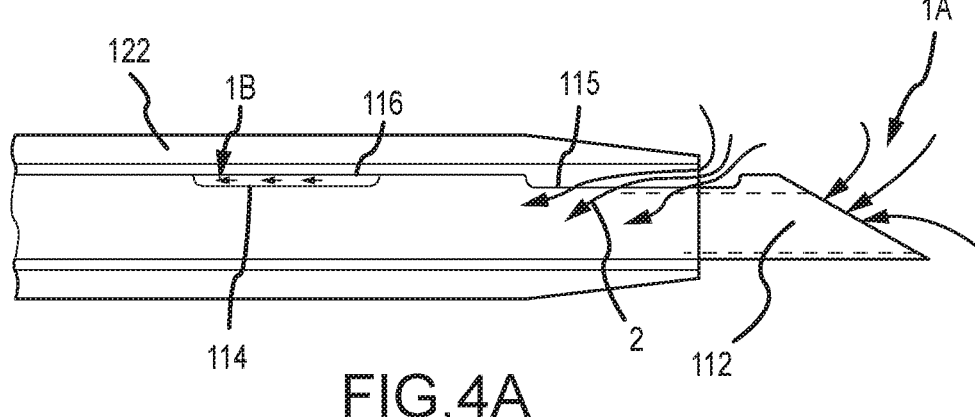
FIG. 4A illustrates a portion of a catheter insertion device in use in accordance with various embodiments, wherein the cannula comprises a fenestration covered with a transparent film seal member to provide a blood viewing window.
Figure 4B:
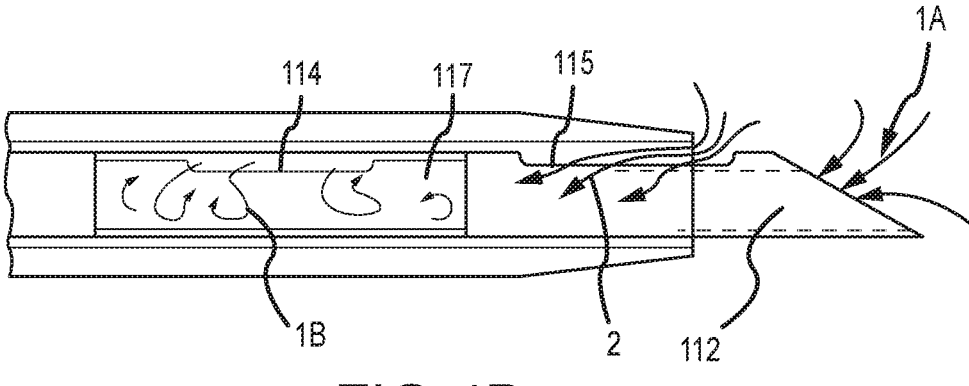
FIG. 4B illustrates a portion of a catheter insertion device in use in accordance with various embodiments, wherein the cannula comprises a fenestration within a segment with a smaller outer diameter, surrounded by a transparent sleeve to provide a blood viewing space around the fenestration while maintaining a consistent outer diameter along the length of the cannula.
Figure 4C:
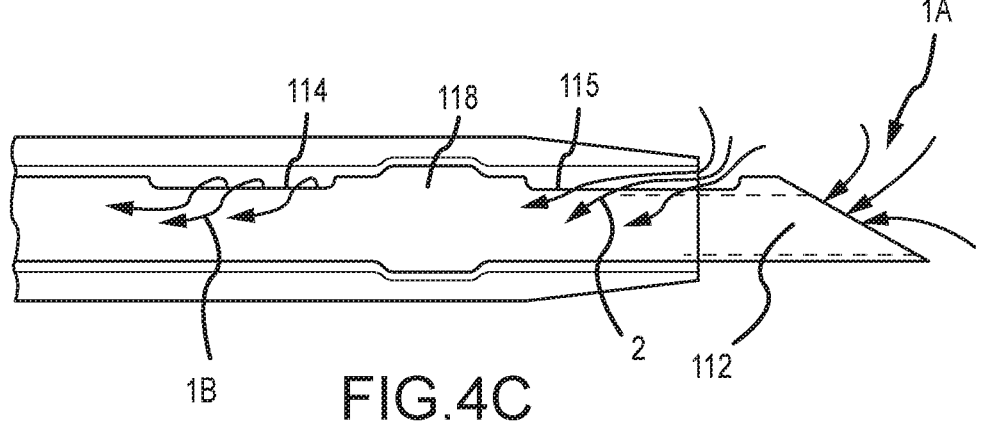
FIG. 4C illustrates a portion of a catheter insertion device in use in accordance with various embodiments, wherein the cannula comprises an open fenestration and an enlarged diameter portion to block distal blood flow emanating from the fenestration and to block proximal blood flow infiltrating from the flat relief portion.

FIGS. 4A-4C generally illustrate various embodiments of a catheter insertion device in accordance with the present disclosure in use. In these illustrations, only the distal end of the device is shown so that the intricacies in the combination of features such as the open fenestration or sealed viewing window, the flat relief portion, the elongated portion, and other aspects of the cannula can be appreciated.

FIG. 4A illustrates an embodiment of a catheter insertion device in use, wherein the cannula 112 includes both a flat relief portion 115 and a fenestration 114 sealed with a transparent film 116. In this illustration, the catheter 122 can be seen to taper at its distal end to essentially form a circumferential seal around the cannula 112. In operation of the embodiments encompassed in FIG. 4A, as blood enters cannula 112 (blood flow indicated as "1A"), blood flash is visible through fenestration 114 (blood flow "1B"). Transparent film 116 sealed over fenestration 114 allows a clinician to visualize blood through this viewing window, with the sealing film preventing blood from flowing out from the fenestration 114 and into the space between cannula 112 and catheter 122. As illustrated in FIG. 4A, flat relief portion 115 enables flash visualization upon catheter entry (with blood flow indicated as "2"). As described herein, flat portion 115 may be configured as illustrated here in FIG. 4A, i.e., terminating just proximal to the bevel of cannula 112. In other embodiments not illustrated, flat portion 115 may extend distally through the beveled distal opening of cannula 112.

With reference to FIG. 4B, a catheter insertion device of the present disclosure may comprise a transparent or translucent cover 117 fit within distal and proximal ends of a narrower diameter portion of the cannula 112, creating a viewing capsule around the fenestration 114. In this way, clinicians can more easily visualize blood within cannula 112 because of the viewing capsule being larger in dimension than the fenestration 114, yet without blood flow out the side of cannula 112 that could cause blood leakage upon cannula withdrawal. In operation, as blood enters cannula 112 (blood flow indicated as "1A"), blood flash is visible through fenestration 114 and the larger viewing capsule provided by the circumferential sleeve 117 (blood flow visible filling in the capsule indicated as "1B"). Sleeve 117 being a cover to fenestration 114 creates a leak-proof viewing capsule with dimensions larger than the fenestration 114. Flat relief portion 115 enables flash visualization upon catheter entry (blood flow indicated as "2"). As discussed above, in other embodiments not illustrated here in use, cover 117 may comprise an insert that fits within the dimensions of the fenestration 114 remaining concentric with cannula 112 and flush with the outside diameter of the cannula 112, thus providing a viewing window generally having the size of the fenestration 114.

With reference to FIG. 4C, a catheter insertion device of the present disclosure may comprise an enlarged portion 118 located between fenestration 114 and flat portion 115. Enlarged portion 118 can be a portion of cannula 112 that, whether due to formation, deposition, fitting of a ferrule over the outside diameter, or otherwise, has a larger diameter than an adjacent portion of cannula 112. Enlarged portion 118 may be comprised of a material that is the same as, or different from, the material of cannula 112. In operation, as blood enters cannula 112 (blood flow indicated as "1A"), blood flash is visible as blood exits through fenestration 114 and into the concentric space between catheter 122 and cannula 112 (blood flow indicated as "1B"). Enlarged portion 118 in cannula 112 prevents blood exiting through fenestration 114 from flowing distally. Flat relief portion 115 enables flash visualization upon catheter entry (blood flow through this shunt indicated as "2"), which is on the distal side of the enlarged portion 118 rather than the proximal side of the enlarged portion 118. In this way, the two separate flash events are distinguishable by which side of the enlarged portion 118 the flash is observed.

Figure 4D:
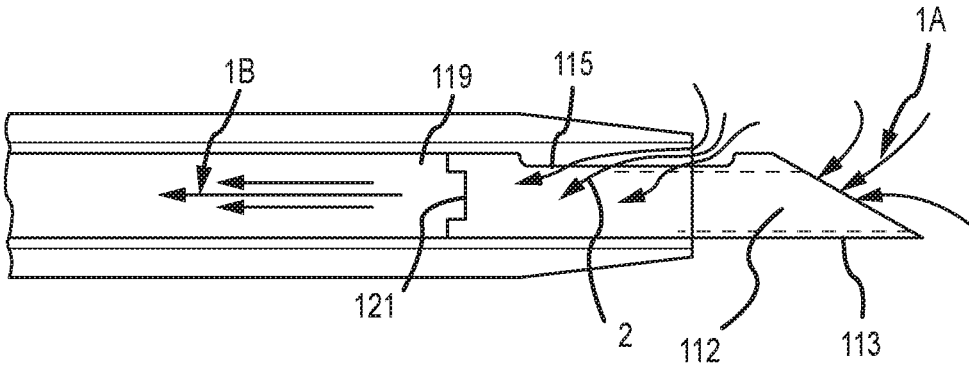
FIG. 4D illustrates a portion of a catheter insertion device in use in accordance with various embodiments, wherein the cannula comprises both nontransparent and transparent tubular portions fit together coaxially in an end-to-end configuration, maintaining consistent outer cannula diameter.

Finally, and with reference to FIG. 4D, cannula comprising proximal and distal segments can connect end-to-end and axially to create a continuous conduit of constant diameter for blood flow therethrough. Proximal segment 119 can comprise a transparent or translucent material, while distal segment 113 can comprises a metallic material or a pigmented plastic otherwise nontransparent. Either using pigmented plastic or metal for the nontransparent distal segment 113 enables sharpening of the open distal end into a sharp tip, such as a beveled end. Proximal segment 119 can be coupled end-to-end to distal segment 113 by overlapping edges frictionally fit or adhered to one another. In some embodiment, overlapping edges may create an enlarged portion 118, as described in various embodiments. In operation, blood enters cannula 112 (blood flow indicated as "1A"), and flows through distal segment 113 into proximal segment 119 of cannula 112 where a clinician can visualize the flow therein (blood flow indicated as "1B"). Proximal segment 119 of cannula being made of a transparent or translucent material allows a clinician the ability to see the blood flowing through. Flat portion 115 enables flash visualization upon catheter entry (blood flow through this shunt indicated as "2").

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips or other means now known in the art or hereinafter developed. Additionally, any reference to without contact (or similar phrases) may also include reduced contact or minimal contact.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A catheter insertion device, comprising:
   a catheter hub including an open proximal end and a distal end having connected thereto a catheter having a distal open end, a through passageway defined by the catheter extends to an interior cavity defined in the catheter hub, the catheter having a circumferential inner wall;
   a septum having a given length having a distal end and a proximal end fitted to the interior cavity of the catheter hub between the distal and proximal ends of the catheter hub;
   a cannula having a beveled distal tip and a circumferential wall defining a lumen an opening at the distal tip, the cannula axially movable through the septum into the interior cavity of the catheter hub and the catheter such that the distal tip of the cannula extends beyond the distal open end of the catheter in a ready position, a fenestration at the circumferential wall of the cannula proximal the distal tip providing an aperture between the lumen and the inner circumferential wall of the catheter, the fenestration having a distal edge and a proximal edge, a distance between the distal tip of the cannula and the proximal edge of the fenestration being greater than the given length of the septum and an other distance between the distal tip of the cannula and the distal edge of the fenestration being greater than a length of the beveled distal tip and less than the given length of the septum;
   a flat relief portion at the cannula extending proximally from the beveled distal tip to a distance distal of the fenestration;
   wherein when the cannula is inserted into a patient and the distal tip of the cannula enters into a vein of the patient, blood flows into the lumen and through the aperture into an annular space defined between the circumferential wall of the cannula and the inner circumferential wall of the catheter to provide a first flashback response, and wherein when the catheter enters the vein, blood flows into a space between the inner diameter of the catheter and the outer diameter of the flat relief portion to provide a second flashback response.

2. The catheter insertion device of claim 1, wherein the fenestration is partially occluded by the septum when the opening at the distal tip of the cannula is moved to within the septum.

3. The catheter insertion device of claim 1, wherein the proximal edge of the fenestration is proximal the proximal end of the septum and the distal end of the fenestration is inside the septum when the opening at the distal tip of the cannula is within the septum.

4. The catheter insertion device of claim 1, wherein the distance between the distal tip of the cannula and the proximal edge of the fenestration is less than or equal to 150% of the given length of the septum.

5. The catheter insertion device of claim 1, wherein the distance between the proximal edge of the fenestration and the distal tip is about 10 mm to about 50 mm.

6. The catheter insertion device of claim 1, wherein the cannula comprises a bump out between the distal tip and the fenestration of the cannula.

7. The catheter insertion device of claim 6, wherein the bump out provides an enlarged transition between the fenestration and the distal tip of the cannula such that blood in the annular space between the circumferential wall of the cannula and the inner circumferential wall of the catheter is blocked from moving distally past the enlarged transition.

8. The catheter insertion device of claim 1, wherein when the cannula is moved proximally relative to the septum such that the distal tip of the cannula is proximal the distal end of the septum, a portion of the fenestration distal its proximal edge is proximal from the proximal end of the septum and another portion of the fenestration proximal its distal edge remains within the septum.

* * * * *